US009187542B2

(12) United States Patent
Grötzinger et al.

(10) Patent No.: US 9,187,542 B2
(45) Date of Patent: Nov. 17, 2015

(54) CILIARY NEUROTROPHIC FACTOR VARIANTS

(75) Inventors: Joachim Grötzinger, Altwittenbek (DE); Stefan Rose-John, Schellhorn (DE); Jürgen Scheller, Neuss (DE); Matthias Aurich, Niebull (DE)

(73) Assignee: CHRISTIAN-ALBRECHTS-UNIVERSITAT ZU KIEL (DE)

( * ) Notice: Subject to any disclaimer, the term of this patent is extended or adjusted under 35 U.S.C. 154(b) by 0 days.

(21) Appl. No.: 14/127,460

(22) PCT Filed: Jun. 13, 2012

(86) PCT No.: PCT/EP2012/061143
§ 371 (c)(1),
(2), (4) Date: Feb. 26, 2014

(87) PCT Pub. No.: WO2012/175378
PCT Pub. Date: Dec. 27, 2012

(65) Prior Publication Data
US 2014/0171620 A1    Jun. 19, 2014

(30) Foreign Application Priority Data
Jun. 18, 2011  (DE) .......................... 10 2011 104 822

(51) Int. Cl.
*C07K 14/475* (2006.01)
*C07K 14/48* (2006.01)
*A61K 38/00* (2006.01)

(52) U.S. Cl.
CPC ............... *C07K 14/48* (2013.01); *C07K 14/475* (2013.01); *A61K 38/00* (2013.01)

(58) Field of Classification Search
None
See application file for complete search history.

(56) References Cited

FOREIGN PATENT DOCUMENTS

| WO | 95/00852 A2 | 1/1995 |
|---|---|---|
| WO | 2005/014641 A2 | 2/2005 |

OTHER PUBLICATIONS

International Search Report and Written Opinion in Corresponding PCT/EP2012/061143 mailed Sep. 20, 2012 (German) (15 pages).
International Search Report in Corresponding PCT/EP2012/061143 mailed Sep. 20, 2012 (English Translation) (4 pages).
Written Opinion of the International Searching Authority in Corresponding PCT/EP2012/061143 mailed Sep. 20, 2012 (English Translation) (7 pages).
International Preliminary Report on Patentability in Corresponding PCT/EP2012/061143 issued Dec. 23, 2013 (English Translation) (8 pages).
Di Marco, et al., "Agonistic and Antagonistic Variants of Ciliary Neurotrophic Factor (CNTF) Reveal Functional Differences between Membrane-bound and Soluble CNTF Alpha-Receptor", The Journal of Biological Chemistry, The American Society for Biochemistry and Molecular Biology, Inc., vol. 272, No. 37, Sep. 12, 1997, pp. 23069-23075 (7 pages).
Saggio, et al., "CNTF Variants with Increased Biological Potency and Receptor Selectivity Define a Functional Site of Receptor Interaction", The EMBO Journal, Oxford University Press, vol. 14 No. 13, pp. 3045-3054, Mar. 13, 1995 (10 pages).
Panayotatos, et al., "Exchange of a Single Amino Acid Interconverts the Specific Activity and Gel Mobility of Human and Rat Ciliary Neurotrophic Factors", The Journal of Biological Chemistry, The American Society for Biochemistry and Molecular Biology, Inc., vol. 268, No. 25, Sep. 5, 1993, pp. 19000-19003 (4 pages).
Schuster, et al., "Signaling of Human Ciliary Neurotrophic Factor (CNTF) Revisited. the Interleukin-6 Receptor Can Serve as an Alpha-Receptor for CNTF", The Journal of Biological Chemistry, The American society for Biochemistry and Molecular Biology, vol. 278, No. 11, Mar. 14, 2003, pp. 9528-9535 (8 pages).

*Primary Examiner* — John Ulm
(74) *Attorney, Agent, or Firm* — Hovey Williams LLP

(57) ABSTRACT

Nucleic acid molecule selected from the group consisting of (a) a nucleic acid molecule having a nucleotide sequence shown in SEQ ID: NO 1, (b) a nucleic acid molecule which encodes a peptide having an amino acid sequence shown in SEQ ID: NO 2, (c) a nucleic acid molecule whose complementary strand hybridizes to a nucleic acid molecule according to (a) or (b) and which codes for a peptide which binds to ciliary neurotrophic factor receptor (CNTFR), the peptide binding with lower affinity than ciliary neurotrophic factor to the interleukin-6 receptor (IL-6R), (d) a nucleic acid molecule whose nucleotide sequence differs from the nucleotide sequence of a nucleic acid molecule according to (c) due to the degenerated genetic code, the codon at positions 82-84 of the nucleic acid molecule according to (a) coding for a non-positively charged amino acid, and the peptide at position 28 shown in SEQ ID: NO 2 having a non-positively charged amino acid residue.

8 Claims, 6 Drawing Sheets

| | |
|---|---|
| hCNTF (SEQ ID NO:7) | MAFTEHSPLTPHRRDLCSRSIWLARKIRSDLTALTESYVKHQGLNKNINLDSADGMPVAS 60 |
| mutCNTF (SEQ ID NO:4) | ------------MDLASRSIWLARKIRSDLTALTESYVKHQGLNKNINLDSADGMPVAS 47 |
| NNTF-1 (SEQ ID NO:6) | ------------MDLASRSIWLARKIESDLTALTESYVKHQGLNKNINLDSADGMPVAS 47 |
| | ** ******************************************** |
| | 63 |
| hCNTF (SEQ ID NO:7) | TDQWSELTEAERLQENLQAYRTFHVLLARLLEDQQVHFTPTEGDFHQAIHTLLLQVAAFA 120 |
| mutCNTF (SEQ ID NO:4) | TDRWSELTEAERLQENLQAYRTFHVLLARLLEDQQVHFTPTEGDFHQAIHTLLLQVAAFA 107 |
| NNTF-1 (SEQ ID NO:6) | TDRWSELTEAERLQENLQAYRTFHVLLARLLEDQQVHFTPTEGDFHQAIHTLLLQVAAFA 107 |
| | ** ******************************************************* |
| hCNTF (SEQ ID NO:7) | YQIEELMILLEYKIPRNEADGMPINVGDGGLFEKKLWGLKVLQELSQWTVRSIHDLRFIS 180 |
| mutCNTF (SEQ ID NO:4) | YQIEELMILLEYKIPRNEADGMPINVGDGGLFEKKLWGLKVLQELSQWTVRSIHDLRFIS 167 |
| NNTF-1 (SEQ ID NO:6) | YQIEELMILLEYKIPRNEADGMPINVGDGGLFEKKLWGLKVLQELSQWTVRSIHDLRFIS 167 |
| | *********************************************************** |
| hCNTF (SEQ ID NO:7) | SHQTGIPARGSHYIANNKKM 200 |
| mutCNTF (SEQ ID NO:4) | SHQTG--------------- 172 |
| NNTF-1 (SEQ ID NO:6) | SHQTG--------------- 172 |
| | ***** |

Fig. 2

CILIARY NEUROTROPHIC FACTOR VARIANTS

RELATED APPLICATIONS

This application is the National Stage of International Patent Application No. PCT/EP2012/061143, filed Jun. 13, 2012, which is hereby incorporated by reference in its entirety, and which claims priority to German Application No. 10 2011 104 822.0, filed Jun. 18, 2011.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

BACKGROUND OF THE INVENTION

1. Field of the Invention

The invention relates to ciliary neurotrophic factor (CNTF) variants which, owing to the loss of affinity for the interleukin 6 receptor (IL-6R), can be used as a therapeutic with particularly low side effects for disorders or diseases which are associated with CNTF.

2. Description of Related Art

During the development of new medicaments which not only reduce weight safely and effectively, but at the same time positively influence metabolic disarrangements which are often associated with adiposity, such as insulin resistance and glucose intolerance, a class of molecules naturally produced by the body has become the subject of current investigation. These molecules are the so-called glycoprotein 130 (gp130) ligands from the group of interleukin (IL)-6-like cytokines, wherein the ciliary neurotrophic factor (CNTF) and its analogs are particularly investigated as potentially active therapeutics against adiposity (Febbraio M A, gp130 receptor ligands as potential therapeutic targets for obesity. J. Clin Invest 2007; 117(4):841-9).

CNTF was originally identified as a trophic factor that supports the survival of neurons in the ciliary ganglion of chick embryos (Adler R, Landa K B, Manthorpe M. Varon S. Cholinergic neuronotrophic factors: intraocular distribution of trophic activity for ciliary neurons. Science 1979; 204 (4400):1434-6). Additional investigations revealed that this effect was not only found with parasympathetic but also with other periphery neurons, such as sympathetic, sensory and motor neurons (Barbin G, Manthorpe M, Varon S. Purification of the chick eye ciliary neuronotrophic factor. J Neurochem 1984; 43(5): 1468-78; Sendtner M, Kreutzberg G W, Thoenen H. Ciliary neurotrophic factor prevents the degeneration of motor neurons after axotomy. Nature 1990; 345 (6274):440-1) and also with different central neurons (Ip N Y, Li Y P, van dS, I, Panayotatos N, Alderson R F, Lindsay R M. Ciliary neurotrophic factor enhances neuronal survival in embryonic rat hippocampal cultures. J Neurosci 1991; 11(10):3124-34; Hagg T, Quon D, Higaki J, Varon S. Ciliary neurotrophic factor prevents neuronal degeneration and promotes low affinity NGF receptor expression in the adult rat CNS. Neuron 1992; 8(1): 145-58; Ip N Y, McClain J, Barrezueta N X, Aldrich T H, Pan L, Li Y, Wiegand S J, Friedman B, Davis S, Yancopoulos G D. The alpha component of the CNTF receptor is required for signaling and defines potential CNTF targets in the adult and during development. Neuron 1993; 10(1):89-102; Clatterbuck R E, Price D L, Koliatsos V E. Ciliary neurotrophic factor prevents retrograde neuronal death in the adult central nervous system. Proc Natl Acad Sci USA 1993; 90(6):2222-6). CNTF is a molecule that has been strongly conserved during evolution and which functions are mainly restricted to the neuromuscular axis (Perret D, Guillet C, Elson G, Froger J, Plun-Favreau H, Rousseau F, Chabbert M, Gauchert J M, Gascan H. Two different contact sites are recruited by cardiotrophinlike cytokine (CLC) to generate the CLC/CLF and CLC/sCNTFRalpha composite cytokines. J Biol Chem 2004; 279(42):43961-70). CNTF shows a number of structural and functional characteristics that distinguish this factor from most other cytokines of the gp130 group. Firstly, it does not possess a signal peptide and consequently cannot be secreted. This led to the early assumption that it is a protein which is stored in the cytosol and released only upon damage of the nerve fibers (Masiakowski P, Liu H X, Radziejewski C, Lottspeich F, Oberthuer W, Wong V, Lindsay R M, Furth M E, Panayotatos N. Recombinant human and rat ciliary neurotrophic factors. J Neurochem 1991; 57(3):1003-12; Stöckli K A, Lottspeich F, Sendtner M, Masiakowski P, Carroll P, Gotz R, Lindholm D, Thoenen H. Molecular cloning, expression and regional distribution of rat ciliary neurotrophic factor. Nature 1989; 342(6252):920-3). Further, CNTF in high concentration is able not only to bind to its original alpha receptor (CNTFR), but also to the IL-6 receptor (IL-6R) (Schuster B, Kovaleva M, Sun Y, Regenhard P, Matthews V, Grotzinger J, Rose-John S, Kallen K J. Signaling of human ciliary neurotrophic factor (CNTF) revisited. The interleukin-6 receptor can serve as an alpha-receptor for CTNF. J Biol Chem 2003; 278(11):9528-35).

Due to its neurotrophic potential, CNTF was tested as a potential therapeutic for different neurodegenerative diseases. Protective effects were shown in animal models (Anderson K D, Panayotatos N, Corcoran T L, Lindsay R M, Wiegand S J. Ciliary neurotrophic factor protects striatal output neurons in an animal model of Huntington disease. Proc Natl Acad Sci USA 1996; 93(14):7346-51; Emerich D F, Winn S R, Hantraye P M, Peschanski M, Chen E Y, Chu Y, McDermott P, Baetke E E, Kordower J H. Protective effect of encapsulated cells producing neurotrophic factor CNTF in a monkey model of Huntington's disease. Nature 1997; 386 (6623):395-9), and a phase I study showed the safety of intracerebrally administered CNTF for Huntington's disease (Bloch J, Bachoud-Levi A C, Deglon N, Lefaucheur J P, Winkel L, Palfi 5, Nguyen J P, Bourdet C, Gaura V, Remy P, Brugieres P, Boisse M F, Baudic S, Cesaro P, Hantraye P, Aebischer P, Peschanski M. Neuroprotective gene therapy for Huntington's disease, using polymer-encapsulated cells engineered to secrete human ciliary neurotrophic factor: results of a phase I study. Hum Gene Ther 2004; 15(10):968-75). In contrast, in a clinical phase III study subcutaneously injected CNTF showed no influence on disease progression in patients with amyotrophic lateral sclerosis (Miller R G, Petajan J H, Bryan W W, Armon C, Barohn R J, Goodpasture J C, Hoagland R J, Parry G J, Ross M A, Stromatt S C. A placebo-controlled trial of recombinant human ciliary neurotrophic (rhCNTF) factor in amyotrophic lateral sclerosis. rhCNTF ALS Study Group. Ann Neurol 1996; 39(2):256-60). Some patients in this study developed a dose-dependent weight loss which confirmed the previously observed cachexia after systemic administration of CNTF to mice (Henderson J T, Seniuk N A, Richardson P M, Gauldie J, Roder J C. Systemic administration of ciliary neurotrophic factor induces cachexia in rodents. J Clin Invest 1994; 93(6):2632-8). Accordingly, work was focused on the elucidation of the mechanisms which lead to such a reduction of the body weight to allow the targeted modulation of these mechanisms. It is however to be concluded that CNTF is not a physiological regulator of the weight, and its cachectic effects were observed exclusively after exogenous administration in animal experiments and clinical studies.

Early on it was already known that CNTF from rats has a fourfold higher activity than human CNTF (Masiakowski P, Liu H X, Radziejewski C, Lottspeich F, Oberthuer W, Wong V, Lindsay R M, Furth M E, Panayotatos N. Recombinant human and rat ciliary neurotrophic factors. J Neurochem 1991; 57(3):1003-12). This is due to an amino acid in position 63 of the protein which is arginine (R) in rats and glutamine (Q) in humans. By the substitution Q63R, it was possible to generate a human CNTF variant whose activity corresponds to that of rat CNTF (Panayotatos N, Radziejewski E, Acheson A, Pearsall D, Thadani A, Wong V. Exchange of a single amino acid interconverts the specific activity and gel mobility of human and rat ciliary neurotrophic factors. J Biol Chem 1993; 268(25):19000-3). Further studies showed that also N-terminal or C-terminal deletions to some extent resulted in an increase of activity or at least did not negatively influence CNTF activity (Negro A, Corsa V, Corona G, Grandi C, Skaper S D, Callegaro L. Structure-function studies of human ciliary neurotrophic factor. Neurochem Res 1994; 19(2):223-7; Krüttgen A, Grotzinger J, Kurapkat G, Weis J, Simon R, Thier M, Schroder M, Heinrich P, Wollmer A, Comeau M. Human ciliary neurotrophic factor: a structure function analysis. Biochem J 1995; 309 (Pt 1):215-20). These findings ultimately led to the generation of Axokine®, a CNTF analog which differs from naturally occurring human CNTF by targeted modifications (deletion of the 15 C-terminal amino acids, replacement of cysteine in position 17 by alanine, and replacement of glutamine in position 63 by arginine) (Peterson W M, Wang Q, Tzekova R, Wiegand S J. Ciliary neurotrophic factor and stress stimuli activate the Jak-STAT pathway in retinal neurons and glia. J Neurosci 2000; 20(11): 4081-90) and which is tested as a potential therapeutic for adiposity (Preti A. Axokine (Regeneron). IDrugs 2003; 6(7): 696-701). Moreover, evidence has been obtained recently that the activity of Axokine® is retained even after simultaneous removal of N- and C-terminal amino acids (Breusing K. Generierung and Charakterisierung eines verbesserten Ciliary Neurotrophic Factors (CNTF). Inauguraldissertation zur Erlangung der Doktorwürde der Medizinischen Fakultät der Christian-Albrechts-Universität zu Kiel 2007).

The CNTF analog Axokine®, developed by the company Regeneron, has already been tested as a potential therapeutic for adiposity. However, in clinical studies the induction of neutralizing antibodies against CNTF has been observed in numerous patients and the substance did not enter the market.

The therapeutic use of CNTF or CNTF analogs, respectively, has been proven problematic so far due to the severe side effects which are associated with their systematic administration. The fact that CNTF in high concentrations is able not only to bind to its original receptor, but also the IL-6R can possibly explain some of the IL-6R-mediated side effects of systemically administered CNTF, such as fever (Shapiro L, Zhang X X, Rupp R G, Wolff S M, Dinarello C A. Ciliary neurotrophic factor is an endogenous pyrogen. Proc Natl Acad Sci USA 1993; 90(18):8614-8) or the induction of an acute phase response in the liver (Dittrich F, Thoenen H, Sendtner M. Ciliary neurotrophic factor: pharmaeokinetics and acute-phase response in rat. Ann Neurol 1994; 35(2):151-63). These effects may be avoided by a monospecifity for the CNTFR.

The induction of neutralizing antibodies against CNTF observed in clinical studies is another so far very problematic aspect when using CNTF as a medicament. These antibodies can both jeopardize the therapeutic effect of the medicament and interfere with the body's own CNTF which is possibly associated with severe consequences. Therefore not only the company Regeneron but also the companies Xencor and Merck have dealt with the mitigation of CNTF immunogenicity (see WO 02/070698 A2; US 2005/0064555 A1 and US 2005/0069987 A1).

Due to the activation of IL-6R CNTF exhibits a B cell and therefore immune stimulating activity. It is hence possible that the pronounced antibody formation that was observed in response to B cell stimulation can be explained by the capability of administered CNTF to bind and activate IL-6R. A CNTF variant which is not able to activate the IL-6R would possibly no longer possess this property. Since on the other hand B cells do not express CNTFR, such a CNTF variant should not be capable of stimulating B cells. It is therefore obvious that the antibody formation against the CNTF variant is prevented in this way.

There is an urgent need for new therapeutics for adiposity and neurological diseases. CNTF variants without affinity or with only low affinity to IL-6R which render it possible to prevent IL-6R-associated side effect are interesting candidates for a new generation of CNTF medicaments for neurological diseases and for the regulation of body weight.

SUMMARY OF THE INVENTION

It is therefore an object of the present invention to provide new CNTF variants without affinity or with low affinity to the IL-6R which can be used as therapeutics without IL-6R-associated side effects. According to the invention, this object is achieved by CNTF variants having the features of a nucleic acid molecule, selected from the group consisting of:
(a) a nucleic acid molecule having the nucleotide sequence depicted in SEQ ID NO: 1,
(b) a nucleic acid molecule which encodes a peptide having the amino acid sequence depicted in SEQ ID NO: 2,
(c) a nucleic acid molecule, whose complementary strand hybridizes to a nucleic acid molecule of (a) or (b) and which encodes a peptide that binds to the ciliary neurotrophic factor receptor (CNTFR), wherein the pep-tide binds to the interleukin-6 receptor (IL-6R) with a lower affinity than the ciliary-neurotrophic factor,
(d) a nucleic acid molecule, whose nucleotide sequence differs from the nucleotide sequence of a nucleic acid molecule of (c) due to the degeneration of the genetic code,
wherein the codon in position 82-84 of the nucleic acid molecule of (a) encodes a non-positively charged amino ac-id, and wherein the peptide has a non-positively charged amino residue in position 28 shown in SEQ ID NO: 2. Advantageous embodiments of the invention are also disclosed.

The CNTF variants according to the invention are CNTF molecules without affinity or with low affinity to the IL-6R so that these molecules will bind to the IL-6R with a lower affinity than the CNTF. This loss in activity is surprisingly achieved by a single amino acid substitution, namely the replacement of the arginine residue in position 28 of human wild-type CNTF (SEQ ID NO: 7) by a non-positively charged amino acid residue. In this way, IL6R-mediated side effects of systemically administered CNTF, such as fever or the induction of an acute-phase response in the liver, can be prevented by the affinity loss to the IL-6R achieved by the invention. The CNTF variants according to the invention should moreover not be able to stimulate B cells so that the formation of antibodies against these CNTF molecules might possibly be prevented. Owing to the possibility of avoiding IL-6R-associated side effects the CNTF variants according to the invention are particularly suitable as CNTF therapeutics.

BRIEF DESCRIPTION OF THE DRAWINGS

The invention will be illustrated in more detail in the figures. The following is shown:

FIG. 2 shows the alignment of the amino acid sequences of human CNTF, mutCNTF and NNTF-1.

DETAILED DESCRIPTION

Subject of the present invention are CNTF variants which recruit the CNTFR as α-receptor but, in contrast to wild-type CNTF, do not interact with the IL-6R or only to a slight extent. This is achieved according to the invention by the substitution of the arginine residue in position 28 of the human wild-type CNTF (SEQ ID NO: 7) by a non-positively charged amino acid residue.

According to the invention, the non-positively charged amino acid residue preferably is an alanine, asparagine, aspartic acid, cysteine, glutamine, glutamic acid, glycine, isoleucine, leucine, methionine, phenylalanine, proline, selenocysteine, serine, threonine, tryptophan, tyrosine or valine residue. According to the invention, the replacement in position 28 of human wild-type CNTF (SEQ ID NO: 7) does not occur by the following positively charged amino acid residues: a histidine or lysine residue.

In a specific embodiment of the invention, the amino acid substitution according the invention occurs in the CNTF variant mutCNTF (SEQ ID NO: 3 and 4). SEQ ID NO: 8 represents the general sequence of the CNTF variants according to the invention based on mutCNTF, in which the replacement of the arginine residue by non-positively charged amino acid residue occurs at position 15. In a preferred embodiment of the invention the arginine (R) in position 28 of human wild-type CNTF (position 15 of mutCNTF) is replaced by glutamic acid (E) (NNTF-1; SEQ ID NO: 5 and SEQ ID NO: 6).

As described in the examples, the inventors have expressed the CNTF variant mutCNTF (SEQ ID NO: 3 and 4) and the R28E-CNTF variant according to the invention (NNTF-1; SEQ ID NO: 5 and 6) in the form of inclusion bodies using a bacterial system, followed by purification and subsequent refolding. Then, the activity was tested on two different BAF/3 cell lines which, apart from the required β subunits, express either CNTFR or the IL6R, thereby providing evidence for specificity for the CNTF variant. The loss in activity is illustrated by the fact that only the interaction of an interleukin with a suitable receptor setting can promote cell proliferation.

Figure 1:
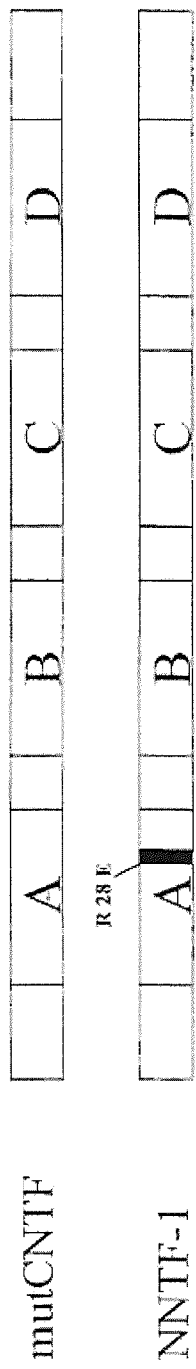
FIG. 1 shows the structure of mutCNTF and NNTF-1.

FIG. 1 shows the proteins mutCNTF and NNTF in the form of so-called ribbon models, wherein the four a helices designated A to D are schematically depicted as the structural feature of the IL-6 family. The CNTF variant mutCNTF used is a modified variant of the CNTF derivative Axokine® (C17A, Q63R, C-terminal deletion of 15 amino acids). Axokine® has a 3- to 5-fold higher effectiveness compared to wild-type CNTF (Preti A. Axokine (Regeneron). IDrugs 2003; 6(7):696-701) and was therefore selected as a basis for these studies. In addition, the N-terminus in mutCNTF was shortened by 14 amino acids. The deletion of the 14 N-terminal amino acids should not affect protein function because they are not part of the α-helix A. Another point mutation was introduced into the CNTF variant NNTF-1 according to the invention which encodes an amino acid replacement in position 28 (R28E, numbering refers to wild-type CNTF; SEQ ID NO: 7) (FIG. 2).

The cDNA of mutCNTF (SEQ ID NO: 3) in the vector pPCR-Script-mutCNTF served as a template for the generation of the NNTF-1 cDNA. Using the primer pairs

Figure 3:
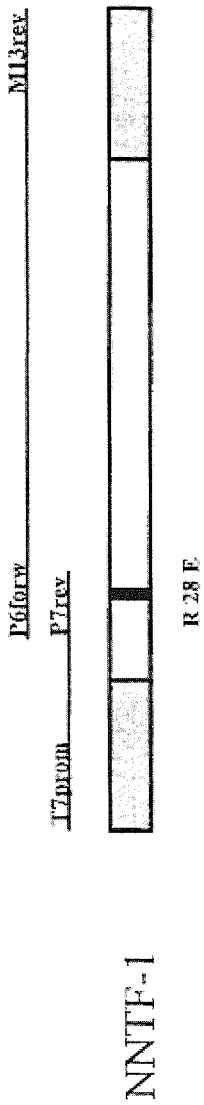
FIG. 3 shows the PCR strategy for generating NNTF-1.

```
T7prom +   [5'-GTAATACGACTCACTATAGGGC-3']        (SEQ ID NO: 9)
P6forw     [5'-CAAGGAAGATTGAGTCAGACCTGACTG-3']   (SEQ ID NO: 10)
and P7rev +    [5'-CAGTCAGGTCTGACTCAATCTTCCTTG-3']   (SEQ ID NO: 12)
M13rev:    [5'-CAGGAAACAGCTATGACCAT-3']          SEQ ID NO: 12)
``` the two 5' and 3' NNTF-1 cDNA fragments were prepared from the cDNA of CNTF in two PCR reactions, and these fragments were joined together to an NNTF-1 cDNA by use of SOE (splicing by overlapping extension) PCR (T7prom+M13rev) (FIG. 3; example 1).

The two C-terminal c-myc and His-tagged recombinant proteins mutCNTF and NNTF-1 were produced as described in example 2.

The activity testing of the proteins mutCNTF and NNTF-1 was performed on the murine cell lines BAF/3 CNTFR-gp130-LIFR and BAF/3 IL-6R-gp130-LIFR, respectively (example 3). Due to a stable transfection these cell lines express, apart from the preceptors gp130 and LIFR, either the CNTFR or the IL-6R as an α-receptor, so that only an interleukin which is capable of interacting with the corresponding receptor setting can promote their proliferation.

Figure 4:
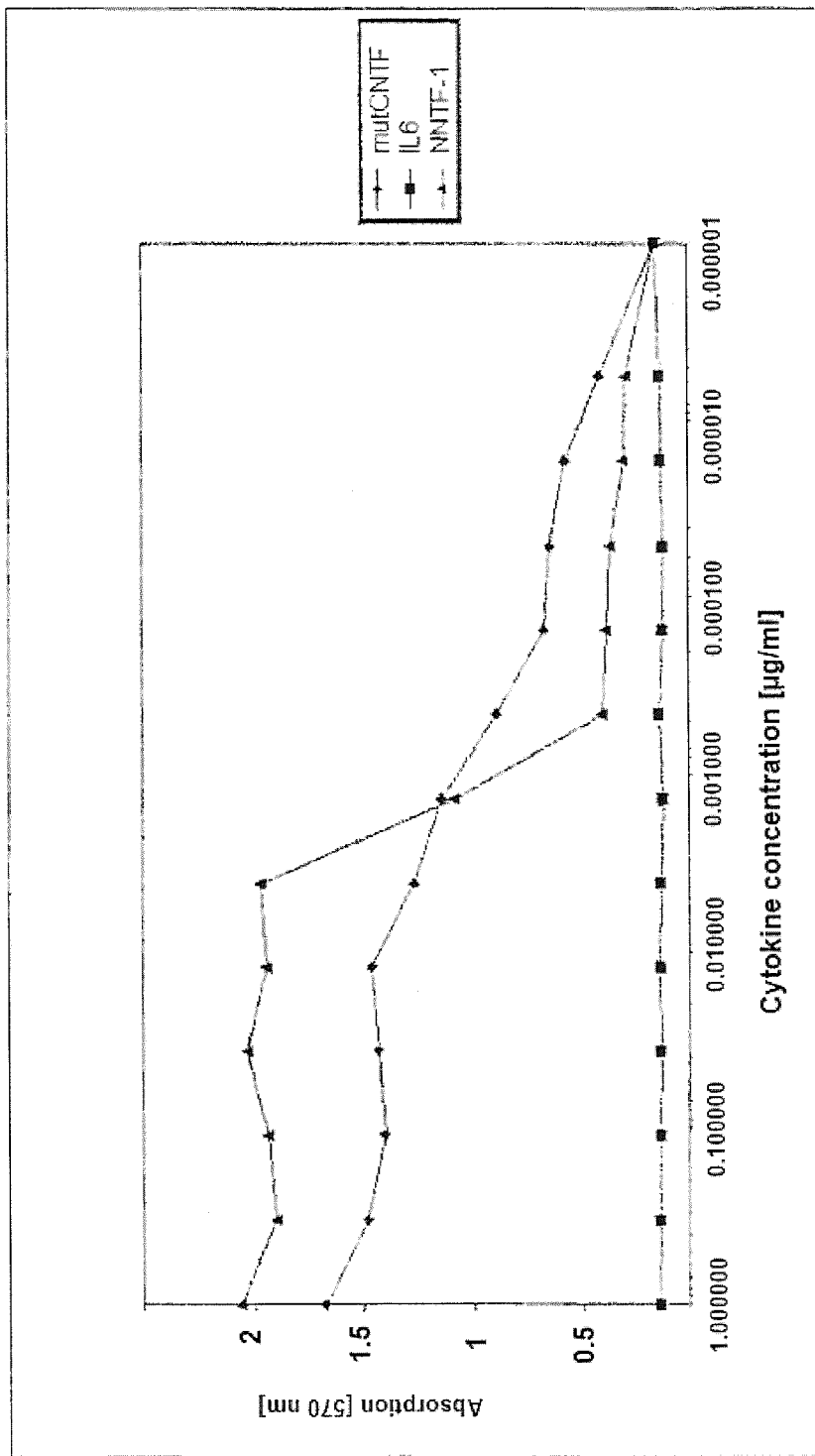
FIG. 4 shows a proliferation assay with BAF/3 CNTFR-gp130-LIFR cells.
Figure 5:
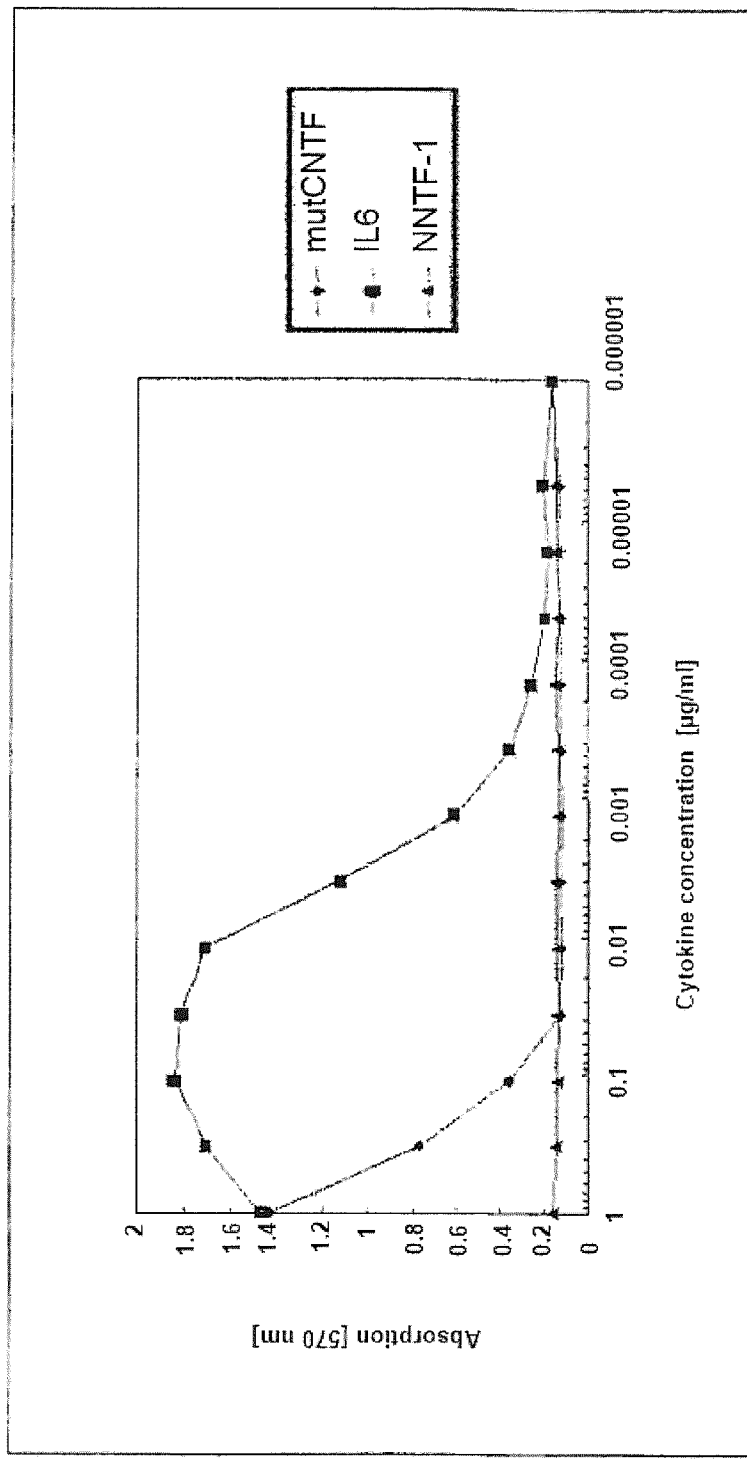
FIG. 5 shows a proliferation assay with BAF/3 IL-6R-gp130-LIFR cells.

FIG. 4 shows the proliferative response of mutCNTF, IL-6 and NNTF-1 on BAF/3 cells which had been stably transfected with CNTFR, gp130 and LIFR (BAF/3 CNTFR-gp130-LIFR), and FIG. 5 shows the proliferative response on BAF/3 cells which had been stably transfected with IL-6Ra, gp130 and LIFR (BAF/3 IL6R-gp130-LIFR). Both cell lines were incubated with increasing concentration of CNTF, IL-6 and NNTF-1 and subsequently subjected to a biochemical proliferation assay. As a measure for cell division, the absorption at 570 nm was photometrically determined and is directly proportional to the number of viable cells. The proliferation assays shown make clear that on the one hand mutCNTF and NNTF-1 are able to stimulate the proliferation of the BAF/3 CNTFR-gp130-LIFR cells, whereas on the other hand only mutCNTF but not NNTF-1 exerts an activity on BAF/3 IL-6R-gp130-LIFR cells. As expected, IL-6 could only stimulate proliferation of BAF/3 IL-6R-gp130-LIFR cells (FIGS. 5 and 5).

Figure 6:
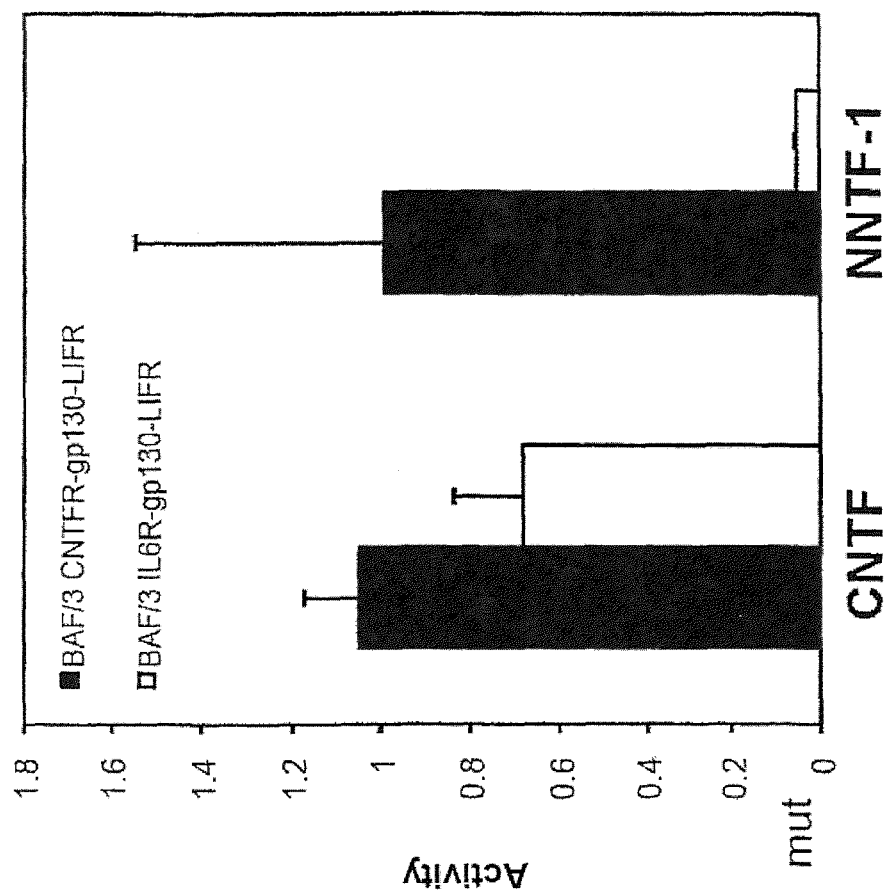
FIG. 6 shows a comparison of the activities of mutCNTF and NNTF-1.

In FIG. 6 NNTF-1 is functionally compared with the originally mutCNTF molecule. As a representative parameter for comparison, the mutCNTF-induced, half-maximal proliferation rate as achieved on BAF/3 CNTFR-gp130-LIFR cells at a cytokine concentration of 0.00137 µg/ml and on BAF/3 IL-6R-gp130-LIFR cells at 0.333 µg/ml (see FIGS. 4 and 5) was used. It becomes clear that compared to mutCNTF, NNTF-1 exerts no significant activity on BAF/3 IL6R-gp130-LIFR cells. In contrast, the activity of NNTF-1 on BAF/3 CNTFR-gp130-LIFR cells is comparable to that of mutCNTF.

To examine whether the desired loss in interaction with the IL6R can be achieved with NNTF-1, this cytokine variant according to the invention was tested in comparison with the two cytokines IL-6 and mutCNTF on the cell lines BAF/3 CNTFR-gp130-LIFR and BAF/3 IL-6R-gp130-LIFR. IL-6 showed the known characteristic of inducing proliferation of BAF/3 IL-6R-gp130-LIFR cells. MutCNTF also had this effect, however, only at higher concentrations. From this, it can be concluded that mutCNTF has affinity to the IL-6R, although this affinity is weak. By contrast, NNTF-1 did not show such an effect even at high concentrations: proliferation and survival of the BAF/3 IL-6R-gp130-LIFR cells could not be stimulated anymore by NNTF-1. Experiments with BAF/3 CNTFR-gp130-LIFR cells showed that these cells expectedly reacted to mutCNTF by proliferation. From these results it can be concluded that NNTF-1, but not mutCNTF, is not able to bind the IL-6R anymore. This could be demonstrated by cell proliferation which only occurs if the ligand binds to its receptor and thereby initiates the intracellular signal cascade. The binding characteristics to CNTFR were not detectably influenced by the amino acid replacement R28E in NNTF-1. Surprisingly, the replacement of a single amino acid is sufficient to reduce the affinity of mutCNTF to the IL-6R such that no cell proliferation is possible anymore. In this way, a central role of the arginine residue 28 of human CNTF in the interaction between the cytokine and the receptor is implied.

Subject of the present invention are therefore nucleic acid molecules that encode CNTF variants, which comprise a non-positively charged amino acid residue instead of the arginine residue in position 28 of human wild-type CNTF (SEQ ID NO: 7).

Apart from the described CNTF peptides, which comprise a non-positively charged amino acid residue instead of the arginine residue in position 28 of human wild-type CNTF (SEQ ID NO: 7), biologically active fragments thereof are also subject of the invention. Biologically active means that the fragments do not have affinity to the IL-6R in the proliferation assay provided in the examples or in any other detection method known to the skilled person and are therefore specific for the CNTFR, just as the underlying full-length peptides. Preferably, they are derivatives which lack one or more amino acids at the N- or C-terminal. However, amino acids from the sequence can also be deleted. Such fragments preferably do not have more than 30% of the amino acids deleted.

Furthermore, CNTF peptides in which single amino acids have been replaced are also subject of the invention. Preferably, the replacements are conservative replacements; i.e. amino acids with similar characteristics are replaces, e.g. alanine by serine, leucine by isoleucine, etc. It is preferred that not more than 10% of the amino acids within the peptides are replaced.

Moreover, single amino acids can also be replaced by non-naturally occurring amino acids, i.e. by amino acids which carry additional functional groups, such as hydroxyproline, methylthreonine, homocysteine, etc. Also in this case, it is preferred that not more than 10% of the amino acids are modified in this manner. Further, the peptides can carry derivatisations, which means that they can be, e.g., amidated, glycosylated, acetylated, sulphated or phosphorylated.

The present invention moreover provides a production method for the peptides of the invention. Apart from genetic engineering of the peptides, the total synthesis on common solid phases in the sense of the Merrifield synthesis or a liquid phase synthesis are likewise possible. The synthesis strategy and the composition of the peptides and derivatives derived therefrom with correspondingly protected amino acids are known to the skilled person.

The present invention also relates to a vector which is characterized by a nucleic acid molecule of the invention, as well as to a host cell which is characterized by a vector of the invention and which is able to express a peptide of the invention.

Host cell, characterized by a vector, characterized by:
a nucleic acid molecule having the nucleotide sequence depicted in SEQ ID NO: 1,
a nucleic acid molecule which encodes a peptide having the amino acid sequence depicted in SEQ ID NO: 2,
a nucleic acid molecule, whose complementary strand hybridizes to a nucleic acid molecule of (a) or (b) and which encodes a peptide that binds to the ciliary neurotrophic factor receptor (CNTFR), wherein the peptide binds to the interleukin-6 receptor (IL-6R) with a lower affinity than the ciliary-neurotrophic factor, or
a nucleic acid molecule, whose nucleotide sequence differs from the nucleotide sequence of a nucleic acid molecule of (c) due to the degeneration of the genetic code,
wherein the codon in position 82-84 of the nucleic acid molecule of (a) encodes a non-positively charged amino acid, and wherein the peptide has a non-positively charged amino residue in position 28 shown in SEQ ID NO: 2.

Alternatively, the non-positively charged amino acid residue is selected from the group consisting of an alanine, asparagine, aspartic acid, cysteine, glutamine, glutamic acid, glycine, isoleucine, leucine, methionine, phenylalanine, proline, selenocysteine, serine, threonine, tryptophane or valine residue. Alternatively, the nucleic acid molecule encodes a peptide which binds to the CNTFR without or with low affinity to IL-6R and having an amino acid sequence which differs from the amino acid sequence depicted in SEQ ID NO: 2 by deletion and/or substitution of at least one amino acid. Alternatively, the nucleotide molecule has the nucleotide sequence depicted in SEQ ID NO: 5.

The present invention also relates to a medicament comprising the peptide of the invention for different therapeutic indications. For this purpose the peptides can be used as highly purified compounds or—if sufficient for the particular use—they can be used in the form of a partially purified peptide mixture or as a mixture of several peptides of the invention.

Another subject of the invention is a medicament comprising a peptide of the invention for treating a disorder or disease associated with CNTF.

Subject of the present invention is therefore also a medicament comprising a peptide of the invention for treating adiposity and diseases which are associated with adiposity, such as adiposity-associated insulin resistance, glucose intolerance, diabetes, hyperglycemia, or hyperinsulinemia and/or for the reduction of body weight.

Subject of the present invention is also a medicament comprising a peptide of the invention for the treatment of neurological disorders or diseases or differentiation disorders or diseases or nerve damage.

Neurological disorders or diseases or differentiation disorders or diseases or nerve damages which are associated with CNTF comprise degenerative diseases, such as retinal degeneration, diseases or disorders which comprise the spinal chord, cholinergic neurons or hippocampus neurons, or diseases or disorders which comprise motoneurons, such as amyotrophic lateral sclerosis or those of the Nervus facialis, such as facial palsy. Other diseases or disorders that can be treated comprise: peripheral neuropathy, Alzheimer's disease, Parkinson's disease, Huntington's chorea or muscular atrophy, which e.g. result from denervation, chronic abuse, metabolic burden and malnutrition, or from a condition such as muscular dystrophy syndrome, congestive myopathy, an inflammatory muscular disease, toxic myopathy, nerve trauma, peripheral neuropathy, medicament- or toxin-induced damage or motoneuropathy. The present invention also relates to diseases or disorders which result from damage of the nerve system, wherein such damage can be caused by a trauma, a surgical intervention, an infarction, an infection, and a malignancy or by exposure to a toxic agent.

Additionally, the invention relates to a medicament for the treatment of adiposity and diseases associated with adiposity and/or for the reduction of body weight and for the treatment of a neurological disorder or disease or a differentiation disorder or disease or nerve damage associated with CNTF comprising a peptide of the invention as at least one of its active ingredients and a pharmacological acceptable carrier.

The invention will be described in more detail in the following examples.

Example 1

Generating a Point Mutation Using Splicing by Overlapping Extension (SOE)-PCR

The SOE-PCR for the generating a point mutation is performed in several steps. In addition to the terminal primers of a normal PCR, two primers are designed which are located at exactly complementary positions of the template DNA and embrace the position of the base triplet to be replaced. Thus, the template is not completely amplified, but instead is amplified in two parts, each with a terminal 5' primer and the 3' primer which comprises the mutation and vice versa. In this way two DNA fragments are generated which can be joined with one another in a final ligation PCR owing to their complementary ends (FIG. 3).

The amplification of the DNA was carried out according to the following scheme:

| | |
|---|---|
| initial denaturation | 95° C./120 s |
| 30 x denaturation | 95° C./60 s |
| annealing | 55° C./60 s |
| extension | 72° C./60 s |
| final extension | 72° C./300 s |

The ligation PCR was carried out using the following conditions:

| | |
|---|---|
| initial denaturation | 95° C./60 s |
| 30 x denaturation | 95° C./60 s |
| annealing | 55° C./120 s |
| extension | 72° C./180 s |
| final extension | 72° C./300 s |

Primer:

```
                                          (SEQ ID NO: 13)
P6forw5'-CAAGGAAGATTGAGTCAGACCTGACTG-3'

(SEQ ID NO: 14)
P7rev5'-CAGTCAGGTCTGACTCAATCTTCCTTG-3'

(SEQ ID NO: 15)
T7prom5'-GTAATACGACTCACTATAGGGC-3'

(SEQ ID NO: 16)
M13rev5'-CAGGAAACAGCTATGACCAT-3'
```

Example 2

Protein Expression and Purification

For protein expression of the inserts NNTF-1 and mutCNTF, which had been cloned in the expression vector pET-23a(+) (Novagen, Gibbstown, USA), the *E. coli* strain BL21(DE3)pLysS (Novagen, Madison, USA) was used. The expression was performed in 1 liter LB medium, wherein said medium had been previously autoclaved and a selection antibiotic had been added. In a first step, colonies of transformed bacteria were picked from an agar plate and incubated overnight in a small volume of 50 ml. Subsequently, 10 ml of this volume were transferred to the expression batch, and the batch was agitated at 180 rpm and 37° C. in an incubator until an $OD_{600}$ of 0.8 was reached. Then, expression was induced with the lactose analog isopropyl S-D-thiogalactopyranoside (IPTG) in a final concentration of 1 mM. After 4 hours the batch was centrifuged for 20 minutes at 4,000 rpm and the pellets were stored at −20° C. in 50 ml centrifugation tubes until purification. The sedimented expression batch was resuspended in a series of 5 repetitions in 100 ml 1×PBS each (initially with the addition of 0.1% (v/v) Tween®20), sonicated on ice three times for one minute using the homogenizer SONOPULS HD 2200 (BANDELIN, Berlin, Deutschland) (30% power) and once again centrifuged for 20 minutes at 15,000 rpm, wherein the supernatant could be discarded. After the last centrifugation step the pellets were resuspended in a total of 12 ml denaturing buffer 1 (6 M GuHCl; 50 mM Tris-HCl pH 8.0). After incubation overnight at room temperature on a roller table the protein solution was centrifuged for 10 minutes at 10,000 rpm and the supernatant was stored at −20° C. until its further processing.

An additional purification was achieved by metal chelate affinity chromatography. 2 ml of Ni-NTA agarose (Qiagen, Hilden, Germany) were used as a supporting material which was washed twice with 10 ml 1×PBS, equilibrated with 10 ml buffer 1 and subsequently loaded with 10 ml protein solution, and the content of the column was incubated on a roller table for 10 minutes at room temperature. After flow through two washing steps were carried out, each with 10 ml buffer 1, and the elution of the proteins was performed with 3×4 ml buffer 2 (6 M GuHCl; 50 mM Tris-HCl pH 8.0; 250 mM imidazole). Successful purification was monitored by SDS-PAGE.

Since the proteins which had been dissolved in GuHCl were present in denatured form, a dialysis was performed in which protein solution [1 mg/ml] was subjected to dialysis in a volume ratio of 1:1000 twice for 12 hours against 50 mM CAPS pH 11.0 at 4° C. The correct folding was verified by CD spectroscopy.

Finally, the FPLC system AKTAexplorer™ (Pharmacia Biotech, Uppsala, Sweden) was used to separate monomeric proteins from aggregated multimeric proteins. After washing the Hiload 16/60 Superdex 75 pg (column volume 120 ml), which was connected to the explorer system, with 120 ml 0.5 M NaOH equilibration was carried out with 240 ml degassed and sterile-filtered 50 mM CAPS pH 11.0, and the column was loaded with 2 ml dialyzed protein solution. During the separation process the proteins were detected at 280 nm. Subsequently, the fractionated elution volume was analyzed by SDS-PAGE and concentrated using centrifugal concentrators (Vivaspin 20, MWCO 10,000; Sartorius, Aubagne, France) to 0.5 to 1 mg/ml.

The two proteins mutCNTF and NNTF-1 were presented as monomers. IL-6 was prepared as described (Fischer, M, Goldschmitt, J, Peschel, C, Brakenhoff, J P, Kallen, K J, Wollmer, A, Grotzinger, J and Rose-John, S I. A bioactive designer cytokine for human hematopoietic progenitor cell expansion. Nat Biotechnol 1997; 15: 142-145).

Example 3

Determination of Activity by Use of a Proliferation Assay

The study of biological activity of NNTF-1 and mutCNTF was performed on two BAF/3 cell lines (48), which had been transfected with the required receptor components:

Cell line: BAF/3 IL-6R-gp130-LIFR
Origin: murine pro-B cells, stably transfected with cDNA for gp130, IL-6R, LIFR
Culturing: in suspension, DMEM+10% FCS+1% P/S, IL-6 [10 ng/ml]
Cell line: BAF/3 CNTFR-gp130-LIFR
Origin: murine pro-B cells, stably transfected with cDNA for gp130, CNTFR, LIFR
Culturing: in suspension, DMEM+10% FCS+1% P/S, CNTF [10 ng/ml]

The cells were washed three times with sterile PBS, counted and resuspended in DMEM (+/+) in a concentration of $5 \times 10^3 / 100$ µl. After addition of the respective cytokines mutCNTF or NNTF-1, 100 µl/well were each pipetted into a 96 well plate and cultured for two days with an increasing concentration series starting with 1 pg/ml and ending with 1 µl/ml cytokine. Then, the proliferation assays were performed. The cells were cultured at 37° C. and a $CO_2$ content of 5%. Proliferation of the cells was measured using the CellTiter-Blue Cell Viability Assay (Promega GmbH, Mannheim) in accordance with the manufacturer's protocol, and the absorption at 570 nm was determined photometrically as the measure for cell proliferation. The absorption is directly proportional to the number of viable cells. All values were determined in triplicate.

The invention claimed is:

1. A nucleic acid molecule, selected from the group consisting of:
   (a) a nucleic acid molecule having the nucleotide sequence depicted in SEQ ID NO: 1, and
   (b) a nucleic acid molecule which encodes a peptide having the amino acid sequence depicted in SEQ ID NO: 2, wherein the codon in position 82-84 of the nucleic acid molecule of (a) encodes a non-positively charged amino acid, and wherein the peptide has a non-positively charged amino residue in position 28 shown in SEQ ID NO: 2, which is glutamic acid.

2. A vector comprising a nucleic acid molecule having the nucleotide sequence according to claim 1.

3. A host cell comprising the vector according to claim 2.

4. A nucleic acid molecule having the nucleotide sequence depicted in SEQ ID NO: 5.

5. A host cell comprising a nucleic acid molecule having the nucleotide sequence according to claim 4.

6. A peptide having the amino acid sequence depicted in SEQ ID NO: 2 or in SEQ ID NO: 8, wherein Xaa is glutamic acid.

7. A peptide according to claim 6, wherein the peptide is a cyclic, amidated, acetylated, sulphated, phosphorylated, glycosylated or oxidated derivative.

8. A medicament comprising a peptide according to claim 6.

* * * * *

SEQUENCE LISTING

```
<160> NUMBER OF SEQ ID NOS: 16

<210> SEQ ID NO 1
<211> LENGTH: 603
<212> TYPE: DNA
<213> ORGANISM: Homo sapiens
<220> FEATURE:
<221> NAME/KEY: misc_feature
<222> LOCATION: (82)..(84)
<223> OTHER INFORMATION: n is a, c, g, or t, whereby the Codon in
      position 82-84 encodes a non-positively charged amino acid

<400> SEQUENCE: 1
atggctttca cagagcattc accgctgacc cctcaccgtc gggacctctg tagccgctct      60
atctggctag caaggaagat tnnntcagac ctgactgctc ttacggaatc ctatgtgaag     120
catcagggcc tgaacaagaa catcaacctg gactctgcgg atgggatgcc agtggcaagc     180
actgatcagt ggagtgagct gaccgaggca gagcgactcc aagagaacct tcaagcttat     240
cgtaccttcc atgttttgtt ggccaggctc ttagaagacc agcaggtgca ttttacccca     300
accgaaggtg acttccatca agctatacat acccttcttc tccaagtcgc tgcctttgca     360
taccagatag aggagttaat gatactcctg aatacaaga tcccccgcaa tgaggctgat     420
gggatgccta ttaatgttgg agatggtggt ctctttgaga agaagctgtg gggcctaaag     480
gtgctgcagg agctttcaca gtggacagta aggtccatcc atgaccttcg tttcatttct     540
tctcatcaga ctgggatccc agcacgtggg agccattata ttgctaacaa caagaaaatg     600
tag                                                                  603

<210> SEQ ID NO 2
<211> LENGTH: 200
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa designates every non-positively charged
      amino acid residue
```

<400> SEQUENCE: 2

```
Met Ala Phe Thr Glu His Ser Pro Leu Thr Pro His Arg Arg Asp Leu
1               5                   10                  15

Cys Ser Arg Ser Ile Trp Leu Ala Arg Lys Ile Xaa Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
        195                 200
```

<210> SEQ ID NO 3
<211> LENGTH: 519
<212> TYPE: DNA
<213> ORGANISM: artificial
<220> FEATURE:
<223> OTHER INFORMATION: DNA sequence encoding the CNTF variant mutCNTF

<400> SEQUENCE: 3

```
atggacctcg cgagccgctc tatctggcta gcaaggaaga ttcgttcaga cctgactgct    60
cttacggaat cctatgtgaa gcatcagggc ctgaacaaga acatcaacct ggactctgcg   120
gatgggatgc cagtggcaag cactgatcgt tggagtgagc tgaccgaggc agagcgactc   180
caagagaacc ttcaagctta tcgtaccttc catgttttgt tggccaggct cttagaagac   240
cagcaggtgc attttacccc aaccgaaggt gacttccatc aagctataca tacccttctt   300
ctccaagtcg ctgcctttgc ataccagata gaggagttaa tgatactcct ggaatacaag   360
atcccccgca atgaggctga tgggatgcct attaatgttg gagatggtgg tctctttgag   420
aagaagctgt ggggcctaaa ggtgctgcag gagctttcac agtggacagt aaggtccatc   480
catgaccttc gtttcatttc ttctcatcag actgggtag                          519
```

<210> SEQ ID NO 4
<211> LENGTH: 172
<212> TYPE: PRT
<213> ORGANISM: artificial
<220> FEATURE:
<223> OTHER INFORMATION: amino acid sequence encoding the CNTF variant mutCNTF

```
<400> SEQUENCE: 4

Met Asp Leu Ala Ser Arg Ser Ile Trp Leu Ala Arg Lys Ile Arg Ser
1               5                   10                  15

Asp Leu Thr Ala Leu Thr Glu Ser Tyr Val Lys His Gln Gly Leu Asn
                20                  25                  30

Lys Asn Ile Asn Leu Asp Ser Ala Asp Gly Met Pro Val Ala Ser Thr
            35                  40                  45

Asp Arg Trp Ser Glu Leu Thr Glu Ala Glu Arg Leu Gln Glu Asn Leu
        50                  55                  60

Gln Ala Tyr Arg Thr Phe His Val Leu Leu Ala Arg Leu Leu Glu Asp
65                  70                  75                  80

Gln Gln Val His Phe Thr Pro Thr Glu Gly Asp Phe His Gln Ala Ile
                85                  90                  95

His Thr Leu Leu Leu Gln Val Ala Ala Phe Ala Tyr Gln Ile Glu Glu
            100                 105                 110

Leu Met Ile Leu Leu Glu Tyr Lys Ile Pro Arg Asn Glu Ala Asp Gly
        115                 120                 125

Met Pro Ile Asn Val Gly Asp Gly Gly Leu Phe Glu Lys Lys Leu Trp
    130                 135                 140

Gly Leu Lys Val Leu Gln Glu Leu Ser Gln Trp Thr Val Arg Ser Ile
145                 150                 155                 160

His Asp Leu Arg Phe Ile Ser Ser His Gln Thr Gly
                165                 170

<210> SEQ ID NO 5
<211> LENGTH: 519
<212> TYPE: DNA
<213> ORGANISM: artificial
<220> FEATURE:
<223> OTHER INFORMATION: NA sequence encoding the CNTF variant NNTF-1

<400> SEQUENCE: 5
atggacctcg cgagccgctc tatctggcta gcaaggaaga ttgagtcaga cctgactgct      60
cttacggaat cctatgtgaa gcatcagggc ctgaacaaga acatcaacct ggactctgcg     120
gatgggatgc cagtggcaag cactgatcgt tggagtgagc tgaccgaggc agagcgactc     180
caagagaacc ttcaagctta tcgtaccttc catgttttgt tggccaggct cttagaagac     240
cagcaggtgc attttacccc aaccgaaggt gacttccatc aagctataca tacccttctt     300
ctccaagtcg ctgcctttgc ataccagata gaggagttaa tgatactcct ggaatacaag     360
atcccccgca atgaggctga tgggatgcct attaatgttg gagatggtgg tctctttgag     420
aagaagctgt ggggcctaaa ggtgctgcag gagctttcac agtggacagt aaggtccatc     480
catgaccttc gtttcatttc ttctcatcag actgggtag                            519

<210> SEQ ID NO 6
<211> LENGTH: 172
<212> TYPE: PRT
<213> ORGANISM: artificial
<220> FEATURE:
<223> OTHER INFORMATION: amino acid sequence encoding the CNTF variant
      NNTF-1

<400> SEQUENCE: 6

Met Asp Leu Ala Ser Arg Ser Ile Trp Leu Ala Arg Lys Ile Glu Ser
1               5                   10                  15

Asp Leu Thr Ala Leu Thr Glu Ser Tyr Val Lys His Gln Gly Leu Asn
                20                  25                  30
```

Lys Asn Ile Asn Leu Asp Ser Ala Asp Gly Met Pro Val Ala Ser Thr
                35                  40                  45

Asp Arg Trp Ser Glu Leu Thr Glu Ala Glu Arg Leu Gln Glu Asn Leu
 50                  55                  60

Gln Ala Tyr Arg Thr Phe His Val Leu Ala Arg Leu Leu Glu Asp
 65                  70                  75                  80

Gln Gln Val His Phe Thr Pro Thr Glu Gly Asp Phe His Gln Ala Ile
                 85                  90                  95

His Thr Leu Leu Leu Gln Val Ala Ala Phe Ala Tyr Gln Ile Glu Glu
                100                 105                 110

Leu Met Ile Leu Leu Glu Tyr Lys Ile Pro Arg Asn Glu Ala Asp Gly
                115                 120                 125

Met Pro Ile Asn Val Gly Asp Gly Leu Phe Glu Lys Lys Leu Trp
                130                 135                 140

Gly Leu Lys Val Leu Gln Glu Leu Ser Gln Trp Thr Val Arg Ser Ile
145                 150                 155                 160

His Asp Leu Arg Phe Ile Ser Ser His Gln Thr Gly
                165                 170

<210> SEQ ID NO 7
<211> LENGTH: 200
<212> TYPE: PRT
<213> ORGANISM: Homo sapiens

<400> SEQUENCE: 7

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
                20                  25                  30

Ala Leu Thr Arg Ser Tyr Val Lys His Gln Gly Leu Asn Lys Asn Ile
                35                  40                  45

Asn Leu Asp Ser Ala Asp Gly Met Pro Val Ala Ser Thr Asp Gln Trp
 50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
                115                 120                 125

Leu Leu Glu Tyr Lys Ile Pro Arg Asn Glu Ala Asp Gly Met Pro Ile
                130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
                195                 200

<210> SEQ ID NO 8
<211> LENGTH: 172
<212> TYPE: PRT

```
<213> ORGANISM: artificial
<220> FEATURE:
<223> OTHER INFORMATION: general sequence of CNTF variants of the
      invention which are based on mutCNTF
<220> FEATURE:
<221> NAME/KEY: misc_feature
<222> LOCATION: (15)..(15)
<223> OTHER INFORMATION: Xaa designates every non-positively charged
      amino acid residue

<400> SEQUENCE: 8

Met Asp Leu Ala Ser Arg Ser Ile Trp Leu Ala Arg Lys Ile Xaa Ser
1               5                   10                  15

Asp Leu Thr Ala Leu Thr Glu Ser Tyr Val Lys His Gln Gly Leu Asn
            20                  25                  30

Lys Asn Ile Asn Leu Asp Ser Ala Asp Gly Met Pro Val Ala Ser Thr
        35                  40                  45

Asp Arg Trp Ser Glu Leu Thr Glu Ala Glu Arg Leu Gln Glu Asn Leu
    50                  55                  60

Gln Ala Tyr Arg Thr Phe His Val Leu Leu Ala Arg Leu Leu Glu Asp
65                  70                  75                  80

Gln Gln Val His Phe Thr Pro Thr Glu Gly Asp Phe His Gln Ala Ile
                85                  90                  95

His Thr Leu Leu Leu Gln Val Ala Ala Phe Ala Tyr Gln Ile Glu Glu
            100                 105                 110

Leu Met Ile Leu Leu Glu Tyr Lys Ile Pro Arg Asn Glu Ala Asp Gly
        115                 120                 125

Met Pro Ile Asn Val Gly Asp Gly Gly Leu Phe Glu Lys Lys Leu Trp
    130                 135                 140

Gly Leu Lys Val Leu Gln Glu Leu Ser Gln Trp Thr Val Arg Ser Ile
145                 150                 155                 160

His Asp Leu Arg Phe Ile Ser Ser His Gln Thr Gly
                165                 170

<210> SEQ ID NO 9
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 9
gtaatacgac tcactatagg gc                                           22

<210> SEQ ID NO 10
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 10
caaggaagat tgagtcagac ctgactg                                      27

<210> SEQ ID NO 11
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 11
```

```
cagtcaggtc tgactcaatc ttccttg                                         27

<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
caggaaacag ctatgaccat                                                 20

<210> SEQ ID NO 13
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 13
caaggaagat tgagtcagac ctgactg                                         27

<210> SEQ ID NO 14
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 14
cagtcaggtc tgactcaatc ttccttg                                         27

<210> SEQ ID NO 15
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 15
gtaatacgac tcactatagg gc                                              22

<210> SEQ ID NO 16
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 16
caggaaacag ctatgaccat                                                 20
```